United States Patent [19]

Steyn et al.

[11] Patent Number: 5,047,167

[45] Date of Patent: Sep. 10, 1991

[54] CLEAR VISCOELASTIC DETERGENT GEL COMPOSITIONS CONTAINING ALKYL POLYGLYCOSIDES

[75] Inventors: Peter L. Steyn, West Orange; Robert Corring, Rockaway Township, Morris County, both of N.J.

[73] Assignee: Lever Brothers Company, Division of Conopco, Inc., New York, N.Y.

[21] Appl. No.: 139,355

[22] Filed: Dec. 30, 1987

[51] Int. Cl.$^5$ .................. C11D 3/37; C11D 3/12; C11D 3/22; C11D 17/00

[52] U.S. Cl. .................... 252/160; 252/173; 252/174; 252/174.17; 252/174.24; 252/174.25; 252/DIG. 14

[58] Field of Search ........... 252/135, 140, 173, 174.14, 252/174.17, 174.24, 174.25, DIG. 14, 156, 160, 174

[56] References Cited

U.S. PATENT DOCUMENTS

| | | | |
|---|---|---|---|
| 2,798,053 | 7/1957 | Brown | 260/2.2 |
| 3,060,124 | 10/1962 | Ginn | 252/135 |
| 3,558,496 | 1/1971 | Zmoda | 252/95 |
| 3,579,455 | 5/1971 | Sabatelli et al. | 252/135 |
| 3,609,102 | 9/1971 | Schlossman | 252/522 |
| 3,720,621 | 3/1973 | Smeets | 252/135 |
| 3,721,633 | 3/1973 | Ranauto | 252/527 |
| 3,896,056 | 7/1975 | Benjamin et al. | 252/539 |
| 3,898,186 | 8/1975 | Mermelstein et al. | 252/528 |
| 4,116,849 | 9/1978 | Leikhim | 252/103 |
| 4,130,501 | 12/1978 | Lutz et al. | 252/186 |
| 4,147,652 | 4/1979 | Kaniecki | 252/156 |
| 4,215,004 | 7/1980 | Borgerding et al. | 252/156 |
| 4,226,736 | 10/1980 | Bush et al. | 252/135 |
| 4,228,048 | 10/1980 | Tesdahl | 260/17.4 |
| 4,240,921 | 12/1980 | Kaniecki | 252/156 |
| 4,260,528 | 4/1981 | Fox et al. | 252/525 |
| 4,396,520 | 8/1983 | Payne et al. | 252/89.1 |
| 4,431,559 | 2/1984 | Ulrich | 252/99 |
| 4,483,780 | 11/1984 | Llenado | 252/135 |
| 4,511,487 | 4/1985 | Pruhs et al. | 252/99 |
| 4,512,908 | 4/1985 | Heile | 252/160 |
| 4,536,317 | 8/1985 | Llenado et al. | 252/174.17 |
| 4,536,318 | 8/1985 | Cook et al. | 252/174.17 |
| 4,565,647 | 1/1986 | Llenado | 252/354 |
| 4,597,886 | 7/1986 | Goedhart et al. | 252/95 |
| 4,606,850 | 8/1986 | Malik | 252/528 |
| 4,654,148 | 3/1987 | Shepherd | 252/91 |
| 4,732,696 | 3/1988 | Urfer | 252/174.17 |

FOREIGN PATENT DOCUMENTS

| | | |
|---|---|---|
| 59-36198 | 2/1984 | Japan . |
| 59-36200 | 2/1984 | Japan . |
| WO83/03621 | 10/1983 | PCT Int'l Appl. . |
| 2116199 | 9/1983 | United Kingdom . |
| 2140450 | 11/1984 | United Kingdom . |
| 2163447 | 2/1986 | United Kingdom . |
| 2163448 | 2/1986 | United Kingdom . |
| 2164350 | 3/1986 | United Kingdom . |
| 2176495 | 12/1986 | United Kingdom . |

OTHER PUBLICATIONS

J. Ferry, "Viscoelastic Properties of Polymers", Third Edition, John Wiley & Sons, New York, 1980.

Akkerman, J., "A Cross—Linking Mechanism of Polyacrylates with Aluminum Compounds", Congr. FATIPEC, 1984, 17 (3), 155-73.

Greenburg, A. and Qckusy, R., "Dynamic Properties of Cross—Linked Poly(acrylic acid)—Aluminum Oxide Composites", J. Mater. Sci., 1980, 15 (12), 3159-62.

B. F. Goodrich Technical Bulletin on Carbopol.

Bulletin and Technical Data from the A. E. Staley Manufacturing Company on Alkylpolyglycosides.

Primary Examiner—Paul Lieberman
Attorney, Agent, or Firm—Milton L. Honig

[57] ABSTRACT

An aqueous cleaning composition is provided in a gel form having a viscosity on a Haake Rotovisco RV-100 Viscometer at 25° C. under 5 sec$^{-1}$ shear of from about 1,000 to 20,000 cps and under 21 sec$^{-1}$ shear of from about 200 to 5,000 cps, a pH range from 11 to 13, and a steady state viscoelastic deformation compliance $J_e^\circ$ greater than 0.01, and wherein the light transmittance through a sample 2 cm thick is at least 10%. The composition will incorporate a polycarboxylic polymeric thickener, especially a cross-linked polyacrylic acid. Also present will be a structurant which can either be up to 2% alumina or up to 0.05% hectorite clay. Also present in the composition will be from 0.01 to 20% of an alkyl polyglycoside which ensures improved cleaning and clarity.

3 Claims, No Drawings

CLEAR VISCOELASTIC DETERGENT GEL COMPOSITIONS CONTAINING ALKYL POLYGLYCOSIDES

BACKGROUND OF THE INVENTION

1. Field of the Invention

The invention relates to a detergent composition in gel form having improved clarity, the compositions being useful for the cleaning of hard surfaces.

2. The Prior Art

Detergents such as those for automatic dishwashing have traditionally been in powder or granulate form. More recently, the marketplace has seen the advent of liquid forms of automatic dishwashing products. Liquids have advantages over powders in their convenience of dispensing or dosing, their enhanced solubility, absence of lump formation or "caking" during storage, and absence of dustiness associated with the powder form.

Problems have been encountered in formulating products for automatic machine dishwashing. These problems arise because the machine dispenser cups have been designed to deliver powders. Chemists have thus been challenged in formulating a liquid product compatible with dispenser cup delivery. There are a number of factors to be considered in such formulations.

Firstly, the composition must be a uniform mixture to deliver an optimum combination of active ingredients to the wash with each dose. Thus, the liquid must possess physical stability against syneresis or physical separation of its active components during storage.

Secondly, a liquid product must be compatible with automatic dishwashing equipment presently available to the consumer. Home dishwashers are fitted with a closed cup to house detergent through several cycles preliminary to the wash cycle. Cups in these machines do not seal tightly and do not adequately retain liquids of low viscosity. Excessive leakage leads to underdosing in the wash cycle. Performance may be adversely affected. Consequently, any liquid product must possess high viscosity to be effectively retained in the cup and avoid leakage into cycles preceding that of the wash.

Conversely, there are situations where the product should have low viscosity. A low viscosity is desirable for easy dispensing of product from its bottle. Thixotropic liquids address the foregoing dilemma by maintaining high viscosity for storage but reverting to lower viscosity under influence of applied shear. Thixotropy is shear thinning behavior that is time dependent in both its decrease in viscosity under applied shear and its regain of viscosity after cessation of shearing.

The earliest approaches to these problems involved the use of clays to modify viscosity. Typical of this technology are the compositions disclosed in U.S. Pat. No. 4,116,849 (Leikhim), U.S. Pat. No. 4,431,559 (Ulrich), GB 2 116 199A (Julemont et al.) and GB 2 140 450A (Julemont et al.). Some patents such as U.S. Pat. Nos. 4,511,487 (Pruhs et al.) and 4,512,908 (Heile) have singled out hectorite as a particularly efficient thickener. There has also been reported in U.S. Pat. No. 3,558,496 (Zmoda) the advantage of combining a negatively charged clay such as hectorite with a positively charged clay such as alumina clay.

GB 2 176 495A suggests the use of polyvalent metal salts of long chain fatty acids, such as aluminum or zinc stearate, as stabilizers against phase separation in a clay laiden liquid composition. Another method of improving phase stability in thixotropic liquids is reported in GB 2 163 448A. This patent suggests inclusion of a limited amount of a water-soluble potassium salt to achieve a potassium: sodium weight ratio of about 0.04 to 0.5. Relatively large crystals are said to be inhibited from forming when potassium is present thereby resulting in greater stability against separation on ageing. U.S. Pat. No. 3,720,621 (Smeets) reports a further useful property of including some potassium salt within a sodium tripolyphosphate liquid composition. Here the presence of potassium allows the amount of sodium tripolyphosphate included within the aqueous detergent to attain a considerably higher solubility than found in the absence of potassium.

Although generally acceptable, clay structured liquids have a number of disadvantages. Montmorillonite clays, even in the presence of stabilizing agents, are sensitive to ionic strength. They lose their liquid structuring efficiency at the high electrolyte levels normally present in autodish liquid detergents. Clays tend to collapse onto themselves, or flocculate under these conditions. If this collapse occurs to any large extend during prolonged storage, the liquid will lose its physical stability, suffer syneresis and/or settling of solids. Collection of solids at the bottom of the container can lead to the formation of paste-like plugs which are difficult to dispense.

Attapulgite clay particles suspended in liquids tend to scatter light. Any large amount of these clay particles will thus impart a muddy dull color to the liquid. Furthermore, clays, being insoluble minerals, can adversely affect glass appearance. Deposition of clay onto the surface of glassware has been known to lead to spotting and filming.

Another problem of suspended solids in prior art liquids is that they are subject to recrystallization during storage periods. Through a process of Ostwald ripening, the solids can redistribute themselves in terms of number and size of crystals. These changes can cause a drastic change in rheology of the liquid over time. Poor stability and/or cup retention result.

Many polymers are known for their thickening properties. Within the machine dishwashing art, polyacrylic acid type polymers have been included as an important component but not necessarily to function as a thickener. Thus, U.S. Pat. No. 3,579,455 (Sabatelli et al.) discusses what is evidently a powdered dishwashing detergent utilizing sodium polyacrylate as an anti-spotting/streaking agent and hardness precipitator. Linear polyacrylate has also been incorporated into thixotropic liquids that have been primarily thickened with powdered clay. GB 2 163 447A (Colarusso) and GB 2 164 350A (Lai et al.) contain such clay-sodium polyacrylate systems and suggest that the polymer provides improved protection to the overglaze layer of fine china. Less filming on glassware was also noted.

Use of polymers for gel-formation in liquid detergent compositions was suggested in U.S. Pat. No. 3,060,124 (Ginn). Apparently, cross-linked vinyl polymers are primarily suitable. Hydrolyzed polyacrylonitrile cross-linked with formaldehyde was found particularly effective at stabilizing the gels against separation. U.S. Pat. No. 4,228,048 (Tesdahl) illustrates the use of polyallyl sucrose cross-linked polyacrylates, commercially available under the trademark Carbopol ®, as a thickener for liquid cleaning and bleaching concentrates. Japanese Laid Open Patents 59-36198 (Kao Soap) and 59-36200

(Kao Soap) further illustrate the use of polyacrylate cross-linked with compounds such as allylated pentaerythritol. These thickened formulas are used to suspend water-insoluble abrasives such as silicone dioxide and aluminum oxide.

Although the aforementioned polymer systems do provide some measure of thickening and phase stabilization, they are frequently not fully adequate at such functions, especially where there is a high level of electrolyte present. Systems are required exhibiting improved stability against phase separation at high electrolyte level and having improved rheological properties. With regard to rheology, the composition must not substantially leak from the cup of an automatic dishwasher, but at the same time be sufficiently shearing to allow flow out of its container.

Liquids including all those of the aforementioned art have another undesirable characteristic. Subsequent to pouring, the mouth of the pouring container will retain flow cut-off product droplets. Normally, these droplets will travel from the lip downward along the outside of the container. Consumers do not like the resulting mess. Some containers have been designed with special pour spouts to prevent this problem. The spouts are, however, quite expensive and not normally used for small-sized containers. It would therefore be desirable to obtain a product inherently having non-drip properties.

There has also been a search for more aesthetically pleasing product forms. Clay structurants cream the carrier liquid resulting in an opaque product. Many polymers also impart opaque properties. Clear compositions would, by contrast, be more aesthetically pleasing to the consumer.

There have been disclosed in co-pending applications Ser. No. 07/139,490, now U.S. Pat. No. 4,836,948 and 07/139,492 cleaning compositions in gel form characterized by a clarity approaching transparency. As is common for most cleaning compositions, it is desirable to include therein a surfactant. Unfortunately, many conventional surfactants when included in the formulation have been found to cause a loss in clarity. For instance, the well-known nonionic surfactant Polytergent SLF-18 ® severely reduces clarity.

Anionic surfactants such as the alkyldiphenyl ether disulfonates, frequently used in automatic dishwashing compositions, do not adversely affect gel clarity. On the other hand, such anionic materials tend to produce levels of foam which are in excess of what may be controllable through the use of defoamers.

Thus, it is an object of the invention to obtain a composition in gel form having a high degree of clarity.

A further object of the invention is to provide a gel cleaning composition incorporating therein a surfactant.

A still further object of the invention is to provide a gel cleaning composition pourable from a container similar to ordinary liquids but having a recoil elasticity rendering the composition dripless.

Another object of the invention is to provide an automatic dishwashing composition in the form of a clear gel with improved cleaning performance.

Also an object of the invention is to provide an automatic dishwashing composition having reduced spotting and filming with respect to glassware.

These and other objects of the invention will become apparent as further details are provided in the subsequent discussion and Examples.

SUMMARY OF THE INVENTION

An aqueous cleaning composition is provided in a gel form having a viscosity on a Haake Rotovisco RV-100 Viscometer at 25° C. under 5 sec$^{-1}$ shear of from about 1,000 to 20,000 cps and under 21 sec$^{-1}$ shear of from about 200 to 5,000 cps, a pH range from 11 to 13, and a steady state viscoelastic deformation compliance $J_e°$ greater than 0.01, and wherein said composition comprises from 0.01 to 20% of an alkyl polyglycoside.

Use of alkyl polyglycoside within the composition ensures improved cleaning and clarity.

DETAILED DESCRIPTION OF THE INVENTION

The aqueous cleaning compositions of the present invention have several properties which are unusual and surprising. Unlike known gel compositions, the present material has an elastic nature rendering the material non-dripping. When tilting a container upright again after pouring, the discharging gel exhibits a memory, recoiling back into the container without leaving any drop of liquid around the container mouth. The effect is somewhat akin to the action of a yo-yo. Gel elasticity is believed to arise from strong intermolecular entwinning which does not seem to occur in other systems. A physical measure of this elasticity or recoil is $J_e°$, the steady state compliance value. $J_e°$ is derived from steady state viscoelastic deformation measurements performed through well known standard techniques (see J. Ferry, "Viscoelastic Properties of Polymers", Third Edition, John Wiley & Sons, New York, 1980). $J_e°$ reflects the elastic deformation and/or energy stored in the elastic components of a fluid during steady flow. This value identifies the extent to which a fluid rebounds when stress is removed. Rebounding or recoil is a property associated with visual perception of elasticity. The $J_e°$ value should be greater than about 0.01 meters$^2$/Newton, preferably greater than about 0.02 meter$^2$/Newton, and optimally between 0.02 and 0.10.

Gel compositions of this invention must also have acceptable flowability from a container but, when at rest, must be relatively non-flowing. The non-flowing property is important in such areas such as automatic dishwashing detergents. When such a detergent is placed in an automatic dishwashing dispenser cup, the detergent composition should have sufficient structural integrity not to rapidly flow out of the dispenser cup. Thus, gel compositions of this invention should possess under the minimum shear conditions of 5 sec$^{-1}$ at 25° C., a viscosity of from about 1,000 to 20,000 cps, preferably from about 1,500 to 10,000 cps, optimally between 3,000 and 7,000 cps. Under flow conditions represented by the shear rate of 21 sec$^{-1}$ at 25° C., the viscosity should range from about 200 to 5,000 cps, preferably from about 800 to 4,000 cps, optimally from 900 to 2500 cps. The aforementioned viscosities are measured on a Haake Rotovisco RV-100 Viscometer. A pH range for these liquids varies from about 11 to 13.

Another unusual property that certain embodiments of the present invention may possess is that of clarity or near transparency. The term "clear" as used in the specification is intended to connote its usual dictionary definition. Thus, a clear composition allows ready viewing of objects behind it. By contrast, a translucent composition although allowing light to pass through, causes light to be so scattered as by a very small portion of crystals or insolubles, that it will be impossible to clearly identify objects behind the translucent material. Within the context of this invention, the composition is deemed to be clear if the maximum transmittance of light through a sample 2 cm thick is at least 10%, preferably at least 20%, optimally greater than 50%. A gel is deemed translucent if the maximum transmittance of such light through the sample is between 5% and 10%. Finally, a gel is deemed opaque if the maximum transmittance of light is below 5%. This transmittance can easily be measured by placing a sample of the aforestated thickness in the light path probe of a Brinkmann PC 800, Colorimeter fitted with a 470 nm filter. Distilled water is considered a baseline for 100% transmittance.

Cleaning compositions of this invention will contain a surfactant. In order to maintain a gel with a high degree of clarity, it has been found that only certain types of nonionic surfactants are compatible. More particularly, it has been discovered that alkyl polyglycosides impart excellent cleaning while still maintaining clarity of the gel composition. Alkyl glycosides of the present invention correspond to the formula:

$$RO(R'O)_y(Z)_x$$

wherein R is a monovalent organic radical (e.g., a monovalent saturated aliphatic, unsaturated aliphatic or aromatic radical such as alkyl, hydroxyalkyl, alkenyl, hydroxyalkenyl, aryl, alkylaryl, hydroxyalkyl, alkenyl, hydroxyalkenyl, aryl, alkylaryl, hydroxyalkylaryl, arylalkyl, alkenylaryl, arylalkenyl, etc.) containing from about 6 to about 30 (preferably from about 8 to 18 and more preferably from about 9 to about 13) carbon atoms; R' is a divalent hydrocarbon radical containing from 2 to about 4 carbon atoms such as ethylene, propylene or butylene (most preferably the unit $(R'O)_y$ represents repeating units of ethylene oxide, propylene oxide and/or random or block combinations thereof); y is a number having an average value of from 0 to about 12; Z represents a moiety derived from a reducing saccharide containing 5 or 6 carbon atoms (most preferably a glucose unit); and x is a number having an average value of from 1 to about 10 (preferably from 1.5 to about 10 and more preferably from about 1.5 to about 5).

Glycoside surfactants suitable for use herein also include those of the formula above in which one or more of the normally free (i.e., unreacted hydroxyl groups of the saccharide moiety, Z, have been alkoxylated; preferably, ethoxylated or propoxylated) so as to attach one or more pendant alkoxy or poly (alkoxy) groups in place thereof. In such event, the amount of alkylene oxide (e.g., ethylene oxide, propylene oxide, etc.) employed will typically range from about 1 to about 20 (preferably from about 3 to about 10) moles thereof per mole of saccharide moiety within the formula glycoside material.

In glycosides of the formula above, the $RO(R'O)_y$ group is generally bonded or attached to the number 1 carbon atom of the saccharide moiety, Z. Accordingly, the free hydroxyls available for alkoxylation are typically those in the number 2, 3, 4 and 6 positions in 6-carbon atom saccharides and those in the number 2, 3, 4 positions in the 5-carbon atom saccharides species. Typically, the number 2 position hydroxyls in the 5-carbon saccharides, and the number 2 and 6 position hydroxyls in 6-carbon saccharides, are substantially more reactive or susceptible to alkoxylation than those in the number 3 and 4 positions. Accordingly, alkoxylation will usually occur in the former locations in preference to the latter.

Glycoside surfactants especially preferred for use herein include those of the formula above wherein R is an alkyl group containing from about 8 to 18 (especially from about 9 to about 13) carbon atoms; y is zero; Z is glucose or a moiety derived therefrom; and x has an average value of from 1.5 to about 5 (especially from about 1.5 to about 3). It is to be noted that by use of alkyl polyglycosides, there often is no need for any hydrotropes such as urea, ethanol or $C_1$–$C_3$ alkylbenzene sulfonates.

Glycoside surfactants of particular interest for use in the practice of the present invention preferably have a hydrophilic-lipophilic balance (HLB) in the range of from about 10 to about 18 and most preferably in the range of from about 12 to about 14.

Within the compositions of the present claim, alkyl polyglycosides will be present in amounts ranging from about 0.01 to about 20% by weight, preferably from about 0.5 to about 10%, optimally between about 1 and 2%.

Commercially, alkyl polyglycosides are available from the Horizon Chemical Company, a subsidiary of the A. E. Staley Manufacturing Company. These materials are sold under the trademark APG. Particularly preferred materials in this category are APG 23-3 and APG 91-3 which are $C_{12}$–$C_{13}$ and $C_9$–$C_{11}$ alcohol glycoside derivatives, respectively, having about three moles of glycosylation.

In one embodiment of the present invention, it has been found that a gel with the aforedescribed unique recoil properties can be obtained by use of a cross-linked polycarboxylate polymer. Desirably, there should also be present a trivalent metal containing material. Moreover, there preferably should be present a structuring chelant.

Polycarboxylic thickening polymers in aqueous media are known to tolerate, without phase separation, modest electrolyte levels in such products as liquid automatic dishwashing detergents. Problems of phase separation will, however, occur when these modest electrolyte levels are substantially increased by the addition of further salts. Thus, according to the first embodiment, it has been found that certain cross-linked polycarboxylic polymers will impart a reasonably high viscosity to liquids even in the presence of high levels of salts.

Further work has indicated that high viscosity alone is insufficient for certain product systems. For instance, automatic dishwashing products require an adequate level of product retention within the cup of a dishwashing machine. For such product applications, it has been found desirable to include small amounts of clays such as hectorite or aluminum containing compounds that will interact with the cross-linked polycarboxylic polymers to substantially improve product rheology.

Dependent upon the chosen polymer and hectorite or aluminum containing compound, it may be desirable to also include a water-soluble structuring chelant. The matrix formed through the interaction of cross-linked polymer, hectorite or aluminum compound and structuring chelant affords a salt tolerant gel unaffected by the presence of alkaline sources, builder salts and other soluble ionic species. The system provides for complete solubility of the foregoing components; the matrix is a highly suspending one. Thereby is achieved the additional benefit of eliminating suspended solids, and the attendant settling separation problems. If desired, significant amounts of light dispersing solids may nevertheless be included in the matrix. Translucent or opaque gels would then result.

The polymeric thickener of the first embodiment of the invention is a polycarboxylic polymer that has been interpolymerized with a multi-vinyl or multi-allylic functionalized cross-linking agent. Preferably, the polycarboxylic polymer is interpolymerized with a polyalkenyl polyether of a polyhydric compound. The polyhydric compound should have at least 4 carbons and 3 hydroxy groups. This type of thickener is described in U.S. Pat. No. 2,798,053 and U.S. Pat. No. 4,130,501, both of which are herein incorporated by reference. More specifically the thickener is a water dispersible copolymer of an alpha-beta monoolefinically unsaturated lower aliphatic carboxylic acid cross-linked with a polyether of a polyol. The polyol may be selected from the group consisting of oligosaccharides, reduced derivatives thereof in which the carbonyl group is converted to an alcohol group, and pentaerythritol. The hydroxy groups of said polyol are etherified with allyl groups, said polyol having at least two allyl groups per polyol molecule. A suitable copolymer is one of acrylic acid with low percentages (0.71 to 1.5%) poly allyl sucrose.

Molecular weights of the cross-linked polymer may range from about 500,000 up to 10,000,000, preferably between 500,000 and 2,000,000, optimally about 1,250,000. Examples of commercially available cross-linked polymers based upon allyl sucrose modified polyacrylic acid are the Carbopol ® resins manufactured by the B. F. Goodrich Chemical Company. These materials include Carbopol 941 ® (m.w. 1,250,000), Carbopol 934 ® (m.w. 3,000,000) and Carbopol 940 ® (m.w. 4,000,000). Most preferred is Carbopol 941 ® which gives the best structuring and clarity.

The polymeric thickener of this invention may be present in an amount from about 0.1 to about 10%, preferably from about 0.5 to 2%, optimally between about 0.7 and 1.5% by weight of the composition.

In conjunction with the polymeric thickener, there may be present a co-structurant such as a hectorite clay or a trivalent metal containing material. With regard to the trivalent metal material, the most effective are those materials containing aluminum, especially aluminum salts or aluminum oxides. Among the inorganic aluminum salts that have been found useful are those with counterions selected from sulfate, chloride, phosphate, nitrate, chlorhydroxide, bromide, carbonate and fluoroborate. Alumina is however the most effective source of aluminum. A most preferred form of this material is boehmite, a crystalline phase of aluminum oxyhydroxide. Especially desirable is a semi-crystalline phase commonly referred to as pseudoboehmite. Aluminosilicates were found not to be effective co-structurants and, for purposes of this invention, are excluded as the trivalent metal ion source. Of course, aluminosilicates (e.g. zeolites) might be present for other purposes, such as for calcium hardness sequestration, in the gel compositions, especially where clarity of the fully formulated product is unnecessary.

Hectorite may be present in amounts from about 0.005 up to 0.1% by weight, preferably from 0.01 up to 0.05%. Alternatively, there may be present trivalent metal containing material in amounts from 0.01 up to 10%, preferably from about 0.1 to about 4%, optimally from about 0.1 to 2% by weight of the composition.

A third desirable element of the gel composition is a water-soluble structuring chelant. Particularly suitable are salts of carbonate, pyrophosphate and mixtures of these two materials. For purposes of product clarity, it is preferable to select potassium as the counterion to the carbonate and/or pyrophosphate. Small amounts of sodium may, however, be tolerated. Thus, the molar ratio of potassium to sodium ion should preferably be greater than 1:1, and optimally greater than 4:1. Under situations where potassium carbonate and potassium pyrophosphate are both present, the relative ratio of these chelants will be from 1:10 to 10:1, preferably from 1:4 to 4:1, optimally about 1:4 to 1:1.5. The amount of chelant may range anywhere from about 1% up to about 60%, preferably between about 15 and 35%, optimally between about 25 and 30% by weight of the composition.

When the gel composition is used as an automatic dishwashing formulation, it will normally also contain an oxidizing agent. Traditionally, liquid dishwashing compositions have for this purpose utilized sodium hypochlorite because it is inexpensive. Other oxidizing agents may, however, be employed. For instance, it is also possible to utilize heterocyclic N-bromo and N-chloro imides such as trichlorocyanuric, tribromocyanuric, dibromo and dichlorocyanuric acids, and salts thereof with water solubilizing cations such as potassium and sodium. An example of a hydrated dichlorocyanurate acid is Clearon CDB 56, a product manufactured by the Olin Corporation. The oxidizing material will be present in the mixture from about 0.1 to 10%, with the most preferred range being from 0.1 to 2% by weight. Preferred concentrations will provide about 0.2 to about 1.5 weight % available chlorine.

Automatic dishwashing detergent compositions based upon this invention will also contain sodium or potassium silicate. This material is employed as a cleaning ingredient, source of alkalinity, metal corrosion inhibitor, and protector of glaze on china tableware. Especially effective is sodium silicate having a ratio of $SiO_2:Na_2O$ from about 1.0 to about 3.3, preferably from about 2 to about 3.2. The silicate may be used in the form of an aqueous liquor or a solid. It will be present from about 0.1 to 25%, more preferably from about 5 to 10% by weight of the composition.

Defoaming of the wash may be accomplished by the presence of any of a number of commercially available defoaming agents. These agents may be of the general type of slightly soluble alkyl carboxylates, alkyl phosphates, hydrocarbon waxes, hydrophobic silicas, silicone defoamers, or many others. In addition to being an effective defoamer, the species must be stable to hypochlorite. The defoamer will optionally be present in the composition from about 0.05% to 5%, preferably from about 0.1 to 1%, and most preferably from about 0.1 to 0.5% by weight of the composition. Particularly preferred defoaming agents are polysiloxanes in an emulsified form which are available from Dow Corning and Union Carbide under the trademarks DB-100 and SAG 1000, respectively.

Amounts of water present in the liquid compositions should neither be so high as to produce unduly low viscosity and fluidity, nor so low as to produce unduly high viscosity and low flowability, thixotropic properties in either case being diminished or destroyed. Water will generally be present in an amount ranging from about 25 to 80%, preferably from about 45 to 75%, optimally from about 55 to 65% by weight of the composition.

An alkali metal hydroxide will be used as an alkaline source and as a means to boost the pH to stabilize hypochlorite. Although small amounts of sodium hydroxide may be utilized, this material is desirably excluded in favor of potassium hydroxide. The potassium hydroxide may be added in the form of an aqueous liquor or as a solid. Amounts of potassium hydroxide will range from about 0.1 to 10%, preferably about 0.5 to 5%, and optimally about 1 to 2% by weight of the composition.

Minor amounts of various other adjuvants may be present in the gel composition. Thus, the compositions may include perfumes, flow control agents, soil suspending agents, antiredeposition agents, anti-tarnish agents, enzymes and other functional additives.

Although the gels of this invention have been specifically designed for automatic dishwashing compositions and the foregoing specification has detailed such formulated products, it must be emphasized that the base gel structure can be utilized for other purposes. Thus, it is envisioned that the gel composition of this invention may be useful in products such as fabric washing formulations, hand dishwashing liquids, toilet bowl scrubs, pot/pan cleaners, fabric softeners, denture cleaners and even shampoos.

The following examples will more fully illustrate the embodiments of this invention. All parts, percentages and proportions referred to herein and in the appended claims are by weight unless otherwise indicated.

EXAMPLES 1-9

Gel formulations having the viscosity and $J_e^\circ$ values of the present invention are outlined in the following Table. These formulations vary in the type and amount of surfactant utilized, and also in the antifoam present.

TABLE I

| Component | 1 | 2 | 3 | 4 | 5 | 6 | 7 | 8 | 9 | 10 |
|---|---|---|---|---|---|---|---|---|---|---|
| Water | 55.4 | 55.9 | 55.9 | 55.9 | 56.4 | 56.4 | 55.4 | 56.4 | 55.9 | 55.9 |
| Potassium hydroxide | 1.0 | 1.0 | 1.0 | 1.0 | 1.0 | 1.0 | 1.0 | 1.0 | 1.0 | 1.0 |
| Tetrapotassium pyrophosphate | 19.0 | 19.0 | 19.0 | 19.0 | 19.0 | 19.0 | 19.0 | 19.0 | 19.0 | 19.0 |
| Catapal D alumina | 0.1 | 0.1 | 0.1 | 0.1 | 0.1 | 0.1 | 0.1 | 0.1 | 0.1 | 0.1 |
| Sodium tripolyphosphate | 1.0 | 1.0 | 1.0 | 1.0 | 1.0 | 1.0 | 1.0 | 1.0 | 1.0 | 1.0 |
| Carbopol 941 | 1.0 | 1.0 | 1.0 | 1.0 | 1.0 | 1.0 | 1.0 | 1.0 | 1.0 | 1.0 |
| Britesil H2O | 7.5 | 7.5 | 7.5 | 7.5 | 7.5 | 7.5 | 7.5 | 7.5 | 7.5 | 7.5 |
| Potassium carbonate | 6.0 | 6.0 | 6.0 | 6.0 | 6.0 | 6.0 | 6.0 | 6.0 | 6.0 | 6.0 |
| APG 23-3 | 2.0 | 1.0 | 1.0 | — | — | — | — | — | — | — |
| APG 91-3 | — | — | — | 1.0 | — | — | — | — | — | — |
| APG 9HDP | — | — | — | — | 1.0 | — | — | — | — | — |
| APG 14HDP | — | — | — | — | — | 1.0 | — | — | — | — |
| SLF-18 | — | — | — | — | — | — | 2.0 | — | — | — |
| Dowfax 2A1 | — | — | — | — | — | — | — | 1.0 | 1.0 | — |
| SAG 1000 | — | 0.5 | — | 0.5 | — | — | — | — | — | — |
| DB 100 | — | — | 0.5 | — | — | — | — | — | 0.5 | — |
| APG 35-H | — | — | — | — | — | — | — | — | — | 1.0 |

Clarity was determined by a measurement of percent transmittance; the higher the transmittance value, the clearer the gel.

From Table II, it is evident that all the various alkyl polyglycosides have a transmittance in excess of 20% which is considered transparent within the context of this invention. Polytergent SLF-18 ®, a commercial commonly available alkoxylated onionic surfactant, when incorporated into the gel base formulation at only 2% caused a severe decrease in percent transmittance.

See Example 7. By contrast, incorporation of 2% APG 23-3 caused no decrease, and in fact, provided a slight increase in percent transmittance relative to the gel base.

TABLE II

| Example | % Transmittance |
|---|---|
| Water | 100.0 |
| Gel base (excluding surfactant and defoamer) | 75.9 |
| 1 | 77.6 |
| 2 | 24.7 |
| 3 | 27.8 |
| 4 | 52.8 |
| 5 | 60.9 |
| 6 | 64.4 |
| 7 | 1.4 |
| 8 | 77.6 |
| 10 | 64.2 |

EXAMPLE 10

Foam is of particular concern with automatic dishwashing compositions. Accordingly, several of the formulations of Table I were measured for their propensity to cause foam. Low foam values are the desired objective.

Measurements of relative foam height levels for various compositions were made using a thermally jacketed foam meter and two types of food soils.

A formulated gel composition is prepared and 2.00 gm. of this is added to 500 ml. of tap water at 45° C., so that a level approximately equal to a dosage of 40 gm. is met. A high shear is then applied at the base of the foam meter by means of a commercial Waring blender for one minute. The blender is then shut off and the wash liquor allowed to settle for one minute before a reading is taken.

Measurements that include soils are also performed whereby the wash liquor is doped with either 2.0 gm. of a butter/dry milk mix, or 10 ml. of an egg yolk solution prepared from a premix of one egg yolk in 100 ml. of water.

Scores are then reported as a measured foam height of a particular composition with or without the presence of a soil, and the difference (D) of a soil-only foam height versus the same soil with a given gel formulation.

TABLE III

| | Foam Height Measurements | | | |
|---|---|---|---|---|
| Soil type | Example | No Soil | Soil | D |
| Egg yolk | — | — | 5 | — |
| | 1 | 5 | 10 | 5 |
| | 2 | 2 | 5 | 0 |
| | 3 | 2 | 4 | −1 |
| | 8 | 14 | 9 | 4 |
| | 9 | 5 | 7 | 2 |
| Butter/dry milk | — | — | 7 | — |
| | 1 | 5 | 11 | 4 |
| | 2 | 0 | 4 | −3 |
| | 3 | 2 | 5 | −2 |
| | 7 | 0 | 4 | −3 |
| | 8 | 14 | 11 | 4 |
| | 9 | 15 | 8 | 1 |

EXAMPLE 11

Illustrated here is the effect of the nonionic surfactant upon glass cleaning performance. Ten (10) dinner plates and ten (10) clean glass tumblers were placed in a Kenmore dishwasher. Forty (40) grams of a 4:1 mixture of margarine and powdered milk were placed in the dishwasher. Plates and glasses were then washed with test liquid or control products. Dishwasher dispenser cups were filled with test liquid or control product at equal volume (approximately 40 grams of granular control versus 60 grams of test liquid). After each cycle, glasses were visually inspected and then placed in another machine. Each glass was numerically rated for spotting and filming on a scale of 0 to 4 (0=best; 4=worst). Values for each glass in each of four runs were averaged together for an overall rating.

TABLE IV

| | Cleaning Performance | |
|---|---|---|
| Example | Average Spotting | Average Filming |
| 1 | 2.21 | 0.68 |
| 2 | 1.62 | 2.07 |
| 7 | 1.05 | 2.52 |

EXAMPLE 12

Elastic rebound or recoil properties are discussed in this Example. Viscoelasticity properties were measured using a Carrimed Control Stress Rheometer type 5010 operated in the Creep Mode. A cone-and-plate geometry was employed. Cone radius was 3 centimeters and cone angle was 2°. In the Creep Mode, a constant stress is applied to the sample during which sample deformation is traced over a period of time. This deformation typically has two components for a viscoelastic fluid. The viscous component increases linearly with time while the viscoelastic component rises at a rate which decreases with time, eventually reaching the steady state value. The steady state viscoelastic deformation can be used to define the steady state compliance $J_e^\circ$.

TABLE V

| Component | Amount (grams) |
|---|---|
| Water | 55.4 |
| Potassium hydroxide | 1.0 |
| Tetrapotassium pyrophosphate | 19.0 |
| Catapal D alumina | 0.1 |
| Sodium tripolyphosphate | 1.0 |
| Carbopol 941 | 1.0 |
| Britesil H2O | 7.5 |
| Potassium carbonate | 6.0 |

The $J_e^\circ$ value for Example 12 whose formula appears above was measured to be 0.025. By comparison, commercial clay-based automatic dishwashing liquids have a $J_e^\circ$ value of around 0.0025 which indicates them to be non-elastic and without any rebound or to have dripless properties.

Formulation 12 also is characterized by a viscosity at 5 sec$^{-1}$ shear of 6193 cps and at 21 sec$^{-1}$ shear of 1956 cps as measured on a Haake Rotovisco RV-100 Viscometer at 25° C.

The foregoing description and examples illustrate selected embodiments of the present invention. In light thereof, variations and modifications will be suggested to one skilled in the art, all of which are within the spirit and purview of this invention.

What is claimed is:

1. An aqueous cleaning composition in gel form having a viscosity on a Haake Rotovisco RV-100 Vicsometer at 25° C. under 5 sec$^{-1}$ shear of from about 1,000 to 20,000 cps and under 21 sec$^{-1}$ shear of from about 200 to 5,000 cps, a pH range from 11 to 13, a steady state viscoelastic deformation compliance $J_e^\circ$ value greater than 0.01, and a light transmittance not lower than 10% through a sample 2 cm thick, said composition comprising:
   (i) from 0.1 to 10% of a thickener that is a crosslinked polycarboxylic polymer;
   (ii) from 0.01 to 2% of alumina; and
   (iii) from 0.01 to 20% of an alkyl polyglycoside.

2. A composition according to claim 1, wherein the molecular weight of the polymer ranges from about 500,000 up to 10,000,000.

3. A composition according to claim 1, wherein the molecular weight of the polymer ranges from about 500,000 up to 2,000,000.

* * * * *